(12) United States Patent
Soundararajan

(10) Patent No.: US 10,918,448 B2
(45) Date of Patent: Feb. 16, 2021

(54) SURGICAL TABLE BASE CONSTRUCTION FOR HEAT DISSIPATION FROM HOUSED POWER ELECTRONICS

(71) Applicant: Verb Surgical Inc., Mountain View, CA (US)

(72) Inventor: Vijay Soundararajan, Santa Clara, CA (US)

(73) Assignee: Verb Surgical Inc., Santa Clara, CA (US)

(*) Notice: Subject to any disclaimer, the term of this patent is extended or adjusted under 35 U.S.C. 154(b) by 0 days.

(21) Appl. No.: 16/384,514

(22) Filed: Apr. 15, 2019

(65) Prior Publication Data

US 2019/0374296 A1    Dec. 12, 2019

Related U.S. Application Data

(63) Continuation of application No. 15/473,210, filed on Mar. 29, 2017, now Pat. No. 10,285,766.

(51) Int. Cl.
| | |
|---|---|
| *H05K 7/20* | (2006.01) |
| *H05K 5/00* | (2006.01) |
| *A61B 34/30* | (2016.01) |
| *A61B 34/35* | (2016.01) |
| *A61G 13/10* | (2006.01) |

(52) U.S. Cl.
CPC .............. *A61B 34/35* (2016.02); *A61B 34/30* (2016.02); *A61G 13/10* (2013.01); *H05K 5/0004* (2013.01); *H05K 7/202* (2013.01); *H05K 7/20127* (2013.01); *H05K 7/20136* (2013.01)

(58) Field of Classification Search
CPC .... H05K 7/20009; H05K 7/202; H05K 7/206; H05K 7/20609; H05K 34/30
See application file for complete search history.

(56) References Cited

U.S. PATENT DOCUMENTS

| 5,918,331 A * | 7/1999 | Hall ........................ A61G 1/04 |
| | | 5/626 |
| 7,206,039 B2 * | 4/2007 | Kawamoto ........... G06F 1/1605 |
| | | 348/836 |
| 9,788,647 B2 * | 10/2017 | Joshi ........................ A47B 9/20 |

(Continued)

FOREIGN PATENT DOCUMENTS

WO    WO-2015004067 A1 *    1/2015    ............. A61G 13/06

*Primary Examiner* — Robert J Hoffberg
(74) *Attorney, Agent, or Firm* — Womble Bond Dickinson (US) LLP

(57) ABSTRACT

Some embodiments described herein relate to a surgical table, specifically a base of a surgical table. The surgical table can be adapted to include and/or be coupled to a surgical robot. The base of the surgical table can form an enclosure including a cover and a bottom. Electronic components (e.g., power electronics associated with the surgical robot) can be disposed within the enclosure. In some embodiments described herein, the cover of the base of the surgical table can be constructed of aluminum or similar material having a thermal conductivity of at least 200 W/m K. In some embodiments described herein, a side wall of the base of the surgical table can be constructed of aluminum or similar material having a thermal conductivity of at least 200 W/m K. Other embodiments described herein describe various other solutions for thermal management of electronic components.

19 Claims, 5 Drawing Sheets

(56) References Cited

U.S. PATENT DOCUMENTS

| | | | |
|---|---|---|---|
| 9,925,011 B2* | 3/2018 | Gombert | B25J 9/1666 |
| 10,105,272 B2* | 10/2018 | Giulianotti | A61M 16/20 |
| 10,285,766 B2* | 5/2019 | Soundararajan | H05K 7/20127 |
| 10,555,860 B2* | 2/2020 | Hinton | A61G 1/0212 |
| 2003/0061661 A1 | 4/2003 | Borders | |
| 2005/0228440 A1 | 10/2005 | Brock | |
| 2008/0154159 A1 | 6/2008 | Kwong | |
| 2009/0163928 A1 | 6/2009 | Schena | |
| 2010/0142154 A1 | 6/2010 | Collet | |
| 2010/0152749 A1 | 6/2010 | von Pechmann | |
| 2010/0177478 A1* | 7/2010 | Akalanne | H05K 7/20409 |
| | | | 361/690 |
| 2010/0217260 A1 | 8/2010 | Aramayo | |
| 2011/0008530 A1 | 1/2011 | Woods | |
| 2011/0267780 A1 | 11/2011 | Thrailkill | |
| 2013/0008181 A1 | 1/2013 | Makansi | |
| 2013/0317496 A1 | 11/2013 | Newton | |
| 2015/0116937 A1 | 4/2015 | Huesgen | |
| 2016/0001447 A1 | 1/2016 | Iida | |
| 2016/0081846 A1* | 3/2016 | Katzenstein | A61G 13/00 |
| | | | 607/96 |
| 2016/0089209 A1 | 3/2016 | Parihar | |
| 2016/0120723 A1 | 5/2016 | Giulianotti | |
| 2016/0296293 A1 | 10/2016 | Gill | |
| 2016/0331613 A1 | 11/2016 | Lee | |
| 2017/0022587 A1 | 1/2017 | Adu | |
| 2017/0071693 A1 | 3/2017 | Taylor | |
| 2017/0086834 A1 | 3/2017 | Auld | |
| 2017/0119466 A1* | 5/2017 | Hirvonen | A61B 18/203 |
| 2017/0143429 A1 | 5/2017 | Richmond | |
| 2017/0211815 A1 | 7/2017 | Padula | |
| 2017/0239131 A1 | 8/2017 | Brzenchek | |
| 2018/0014888 A1 | 1/2018 | Bonny | |
| 2018/0036089 A1 | 2/2018 | Nakanishi | |

* cited by examiner

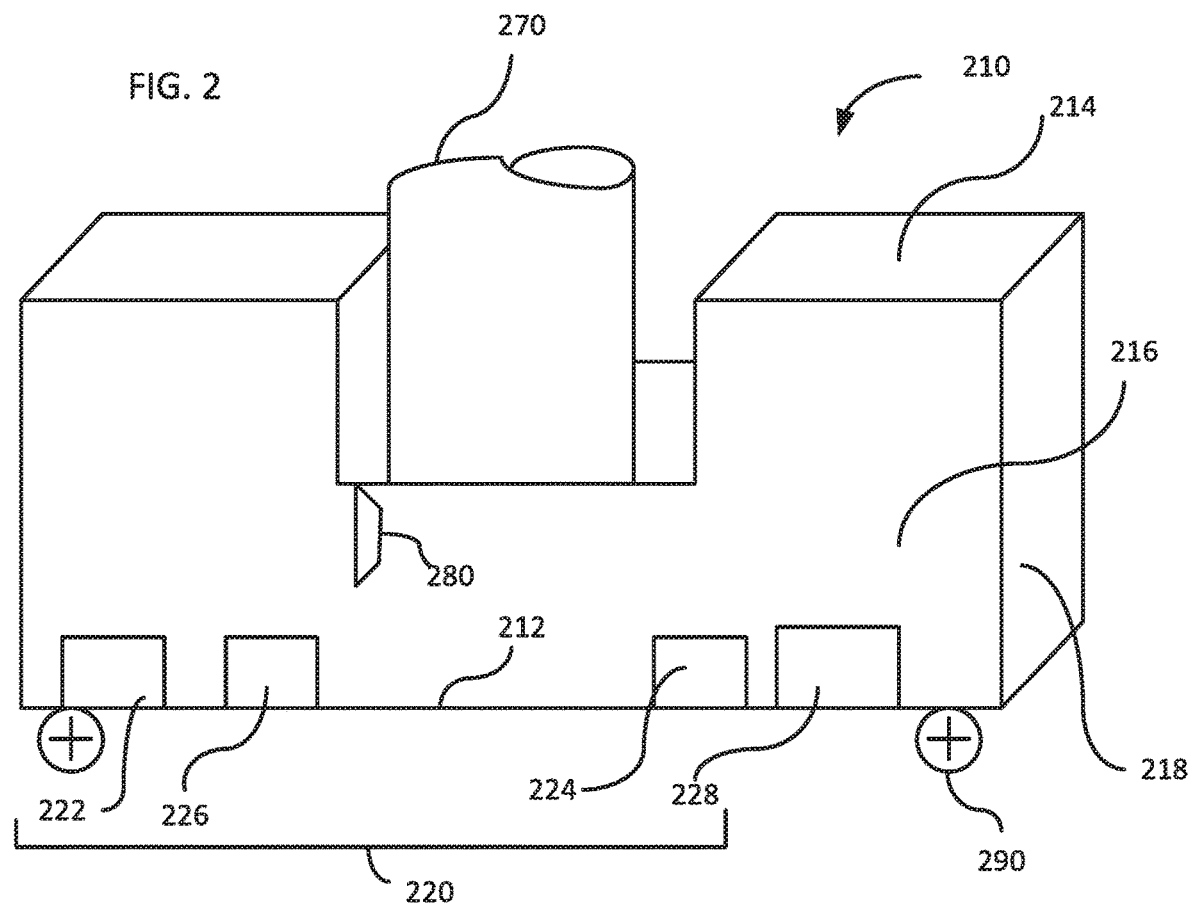
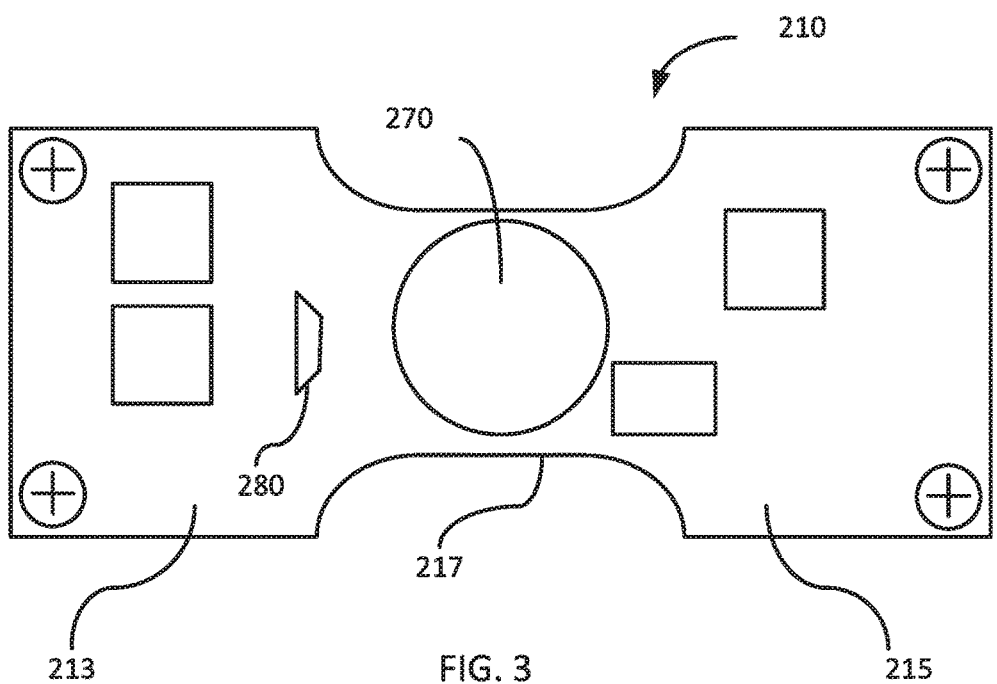

SURGICAL TABLE BASE CONSTRUCTION FOR HEAT DISSIPATION FROM HOUSED POWER ELECTRONICS

CROSS-REFERENCE TO RELATED APPLICATION

The application is a continuation of U.S. patent application Ser. No. 15/473,210, filed Mar. 29, 2017, now issued as U.S. Pat. No. 10,285,766, which is incorporated herein by reference.

BACKGROUND

The present application generally relates to surgical tables, particularly thermal management in surgical tables with power electronics. More specifically, some embodiments described herein relate to surgical tables including or adapted to include one or more surgical robots. Such surgical tables include power electronics associated with the one or more surgical robots, which can produce a significant amount of heat. Some embodiments described herein relate to the management of heat produced by such power electronics.

In many circumstances, surgical tables must comply with a number of safety and performance standards. For example, in some environments the maximum allowable temperature of an external surgical table surface is 45° C. As another example, many surgical tables must be capable of being sprayed with water and, in some instances, must prevent water ingress into or collection in closed areas. Electronics contained within known surgical tables (e.g., height control, tilt control, etc.) are therefore generally disposed within sealed enclosures, such as the base.

Electronic components contained within known surgical tables are relatively low power and therefore produce a relatively modest amount of heat. For example, electronic components contained within known surgical tables might produce approximately 40 W of waste heat. Known surgical tables with such modest heat production do not present thermal management challenges.

Surgical robots generally have greater power consumption and more stringent requirements for clean and/or uninterrupted power than known surgical tables. Moreover, it can be advantageous to provide some or all electronics and/or power electronics associated with surgical robots within a surgical table. The greater power consumption of surgical robots, however, leads to a greater production of waste heat which presents thermal management challenges not present in known surgical tables. A need therefore exists for surgical tables with integrated electronics associated with surgical robots and thermal management technologies for safely dissipating waste heat.

SUMMARY

Some embodiments described herein relate to a surgical table, specifically a base of a surgical table. The surgical table can be adapted to include and/or be coupled to a surgical robot. The base of the surgical table can form an enclosure including a cover and a bottom. Electronic components (e.g., power electronics associated with the surgical robot) can be disposed within the enclosure. In some embodiments described herein, the cover of the base of the surgical table can be constructed of aluminum or similar material having a thermal conductivity of at least 200 W/m K. In some embodiments described herein, a side wall of the base of the surgical table can be constructed of aluminum or similar material having a thermal conductivity of at least 200 W/m K. Other embodiments described herein describe various other solutions for thermal management of electronic components.

BRIEF DESCRIPTION OF THE DRAWINGS

FIG. 2 is a schematic perspective view of a base of a surgical table having electronic components and an internal fan, according to an embodiment.

FIG. 3 is a schematic top view of a base of a base of a surgical table having electronic components, according to an embodiment.

DETAILED DESCRIPTION

Some embodiments described herein relate to a surgical table, specifically a base of a surgical table. The surgical table can be adapted to include and/or be coupled to a surgical robot. The base of the surgical table can form an enclosure including a cover and a bottom. Electronic components (e.g., power electronics associated with the surgical robot) can be disposed within the enclosure. The cover of the base of the surgical table can be constructed of aluminum or similar material having a thermal conductivity of at least 200 W/m K.

Some embodiments described herein relate to a surgical table, specifically a base of a surgical table. The surgical table can be adapted to include or be coupled to a surgical robot. The base of the surgical table can form an enclosure including a cover, a bottom, and a sidewall. The cover can be constructed of a substantially flat steel casting. The sidewall can be constructed of aluminum or similar material having a thermal conductivity of at least 200 W/m K. Electronic components (e.g., power electronics associated with the surgical robot) can be disposed within the enclosure.

Some embodiments described herein relate to a base of a surgical table having a top and a bottom. The top and the bottom can each include a first lobe and a second lobe. A middle portion of each of the top and the bottom disposed between the first lobe and the second lobe can be narrower than first lobe and the second lobe. Thus, the first lobes of the top and bottom can collectively define a first volume of the base, the second lobes of the top and the bottom can collectively define a second volume of the base, and the middle portions of the top and the bottom can collectively define a middle volume of the base. A column of the surgical table can be coupled to the middle portion of the top in such a manner that the column and/or construction of the middle portion of the top inhibits airflow between the first volume and the second volume. A first power supply operable to provide power to a first surgical robot can be disposed in the first volume, and a second power supply operable to provide power to a second surgical robot can be disposed in the second volume.

Figure 1:
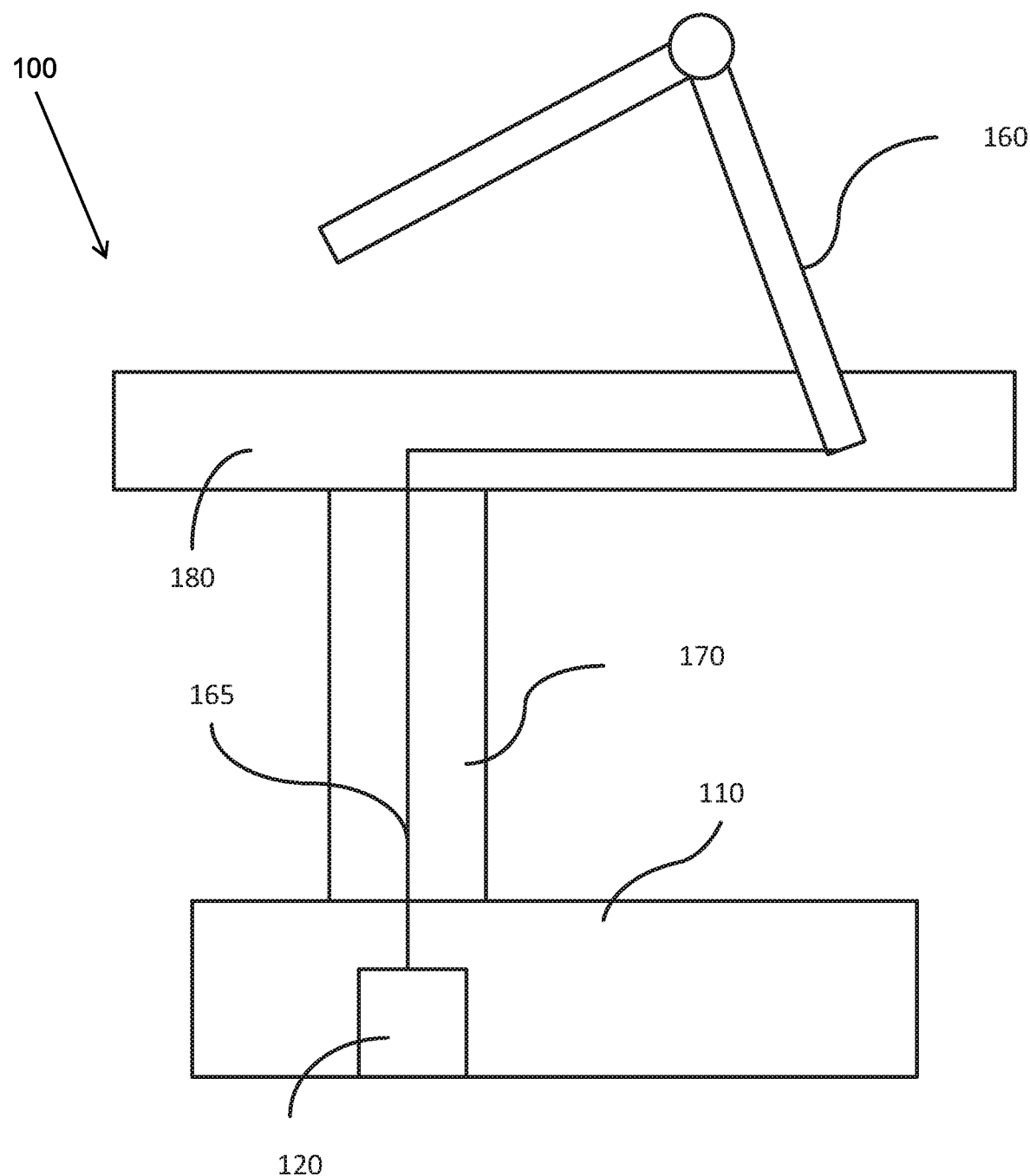
FIG. 1 is a schematic diagram of a surgical table including a surgical robot and electronic components associated with the surgical robot, according to an embodiment.

FIG. 1 is a schematic diagram of a surgical table 100, according to an embodiment. The surgical table 100 includes a base 110, a column 170, and a top 180. The top 180 of the surgical table 100 is adapted to support a patient. The column 170 supports the top 180 and couples the top 180 to the base 110, which is adapted to be in contact with the floor. In some embodiments, the top 180 can be operable to move, tilt, bend, or otherwise articulate or move relative to the base 110. The top 180 and/or the column 170 can include motors, pinions, racks, hydraulics, and/or any other suitable mechanisms and/or actuators operable to articulate and/or move the top 180 of the table 100. In some embodiments, the column 170 can provide an umbilical through which electricity, data, etc. can be transferred between the top 180 and the base 110.

A surgical robot 160 (e.g., a robotic arm, which may support a remote imaging device, radiation source, pump, manipulator, etc.) can be coupled to the surgical table 100. As shown, the surgical robot 160 is coupled to the top 180 of the surgical table 100, but it should be understood that the surgical robot 160 can be coupled to any suitable portion of the surgical table 100. The surgical robot 160 can be removeably coupled to the surgical table 100. In some embodiments, when the surgical robot 160 is coupled to the surgical table 100, the surgical robot can draw power from the surgical table 100, receive commands via the surgical table 100, and/or transmit data via the surgical table 100. Similarly stated, the surgical table 100 can include electrical, data, and/or any other suitable connections suitable for interfacing with the surgical robot 160. The surgical table 100 can further include connections suitable for interfacing with mains power, control systems associated with the surgical robot 160, and/or data monitoring/logging systems, etc. In this way, the surgical table 100 can be operable to transfer input/output between the surgical robot 160 and a power source, a control system, a data monitoring/logging system, etc.

The surgical table 100 can include one or more power electronic components 120. Power electronic components 120 can include batteries, transformers, power conditioning devices, power supplies, and/or any other suitable component generally associated with providing power to the surgical table 100 and/or the surgical robot 160. As shown, the power electronic component 120 is disposed within the base 110 of the table 100. The surgical robot 160, the column 170, and/or the top 180 can be joined to the power electronic component 120 via an electrical connection 165. As shown in FIG. 1, the electrical connection can traverse the column 170.

In some instances, surgical tables, (e.g., the surgical table 100) are subject to a number of regulatory and/or performance requirements. For example, the surgical table 100 may be able to pass a water spray test and/or be suitable to be washed down following a surgical procedure. Such a surgical table 100 can be constructed such that water does not penetrate or collect in closed volumes. For example, any internal volumes associated with the base 110, the column 170, and/or the top 180 can be substantially fluid and/or air tight. For another example, in some instances, the maximum temperature of an exterior surface of the surgical table 100 can be 45° C.

Particularly in embodiments in which the base 110 of the surgical table 100 is fluid and/or air tight, challenges can arise in rejecting waste heat generated by the power electronic component 120. In instances where the power electronic component 120 is a battery, charging and/or discharging the battery can be compromised at temperatures greater than about 48° C.

Embodiments in which the base 110 contains one or more power electronic components 120 associated with the surgical robot 160 can produce substantially more heat than surgical tables that do not include a surgical robot and/or are not configured to have a surgical robot coupled thereto. Similarly stated, surgical tables having only electronic components associated with moving and/or articulating the table itself generally produce significantly less heat than surgical tables including surgical robots. In some embodiments, a surgical table without power electronic components associated with a surgical robot might produce approximately 40 W of waste heat. The surgical table 100, which includes power electronics component 120 associated with surgical robot 160 might produce approximately 150 W of waste heat. Traditional surgical table bases, which can be constructed entirely of steel castings, may be inadequate to reject 150 W of heat without a portion of an exterior surface of the base exceeding 45° C. and/or an interior temperature exceeding 48° C., which may negatively impact battery performance.

Surgical robots (e.g., the surgical robot 160) generally use significantly more power and may require cleaner and/or more stable power supplies than surgical tables themselves. For example, to avoid power interruptions during a surgical procedure, a surgical robot may rely on a battery backup. Moreover, power demands for operating one or more surgical robots can be significantly greater than relatively infrequent power usage by a surgical table to, for example, adjust the orientation of the table top. In addition in some embodiments, the surgical table 100 can include power electronics for multiple surgical robots. In this way, multiple surgical robots, each of which might draw power via an independent set of power electronics, can be used in a surgical procedure. A surgical table having multiple sets of power electronics can result in additional waste heat production and face additional challenges rejecting waste heat.

FIG. 2 is a schematic perspective view of a base 210 of a surgical table, showing a portion of a column 270, according to an embodiment. The base 210 and the column 270 can be structurally and/or functionally similar to the base 110 and/or the column 170, respectively, shown and described above with reference to FIG. 1. The base 210 includes a bottom plate 212, a top cover 214, and a side wall 218 collectively defining an interior volume 216 or enclosure. The top cover 214 can be coupled and/or sealed to the bottom plate 212 in such a manner that the interior volume 216 is substantially fluidically isolated from an exterior volume. Similarly stated, when sprayed with water (e.g., as when subjected to a water spray test and/or as when cleaned after a surgical procedure) the top cover 214, the side wall 218, and the bottom plate 212 can collectively prevent water from entering and/or collecting within the interior volume 216. Such a fluid-tight enclosure, however, can prevent convective heat rejection from the interior volume 216 to the surrounding environment.

One or more electronic components 220 can be disposed within the interior volume 216. Four electronic components 220 are shown in FIG. 2, but it should be understood that this is for illustrative purposes only and the interior volume 216 can include any suitable number of electronic components 220. The electronic components can be, for example, a first power supply 222 to provide power to a first surgical robot (e.g., a transformer and/or power conditioner operable to receive AC power from mains power and provide DC power), a second power supply 228 to provide power to a second surgical robot, a battery 224 operable to provide backup and/or uninterrupted power to the first surgical robot and/or the second surgical robot, and a printed circuit board 226 operable to control operation of the surgical table (e.g., movement via wheels 290, articulation of the top of the surgical table, etc.).

Traditionally surgical table bases are constructed of steel castings having thermal conductivity of approximately 50 W/m K. Bases constructed of steel castings are adequate to reject the relatively small amount of waste heat produced by known tables that—is surgical tables that do not include power electronics components associated with surgical robots—without becoming dangerously hot (e.g., exceeding 45° C.). As the quantity of waste heat produced increases, however, relying on conduction through steel casting alone can result in unacceptable temperatures, such as a portion of the exterior of the base 210 exceeding 45° C. and/or the interior volume 216 reaching or exceeding 48° C., which can negatively impact operation of the battery 224. Base 210, containing the first power supply 222, the second power supply 228, battery 224, and printed circuit board 226, if constructed of steel castings similar to known surgical table bases, may not be able to reject sufficient heat to prevent the exterior of the base 210 from becoming unacceptably hot and/or prevent the battery 224 from overheating.

FIG. 3 is a top view of the surgical table base 210. As shown, the surgical table base has a first lobe 213, a second lobe 215, and a middle portion 217 disposed between the first lobe 213 and the second lobe 215. Consequently, the bottom plate 212 and the top cover 214 each have a first lobe, a second lobe and a middle portion. The length and width of the base 210 can be constrained by access to the patient. For example, the maximum overall length of the surgical table base 210 can be 1550 mm. The maximum width of the first lobe 213 and/or the second lobe 215 can be 650 mm. The height of the base can be constrained by the need to provide clearance allowing surgical robots to move and/or fold beneath the able. The maximum height of the first lobe 213 and/or the second lobe 215 can be 213 mm. The Applicant has discovered that in surgical table bases of similar dimensions, relatively little horizontal convective heat transfer occurs. Rather, waste heat from electronic components tends to rise substantially vertically, creating hot pockets within the interior volume 216. Such hot pockets can produce unacceptably hot local hot spots (e.g., >45° C.) on the surface of the top cover 214 and/or can produce local environments unsuitable for the operation of power electronic components, such as the battery 224.

The column 270 is coupled to the middle portion 217 of the base. The middle portion 217, being both narrower and shorter than the first lobe 213 and the second lobe 215 of the base 210, can further inhibit heat transfer from the first lobe 213 to the second lobe 215 (and vice versa). In some embodiments, the relatively small amount of horizontal heat transfer can be used as an advantage. For example, large heat sources can be balanced. For example, the first power supply 222 can be disposed in one lobe (e.g., the first lobe 213) and the second power supply 228 can be disposed in another lobe (e.g., the second lobe 215). In addition or alternatively, for example, if electronic components 220 in one lobe produce more heat than electronic components 220 in another lobe, a fan 280 can be disposed within the interior volume. The fan 280 can force horizontal heat-transfer by moving air between the first lobe 213 and the second lobe 215, resulting in a more even temperature distribution and decrease of local hot spots or hot pockets that can be dangerous and/or impact electronic component performance.

Alternatively, heat-sensitive components (e.g., the battery 222) can be disposed in the one lobe (e.g., the first lobe 213), optionally with other electronic components that produce a relatively small amount of heat, such as the printed circuit board 226, while components that produce a significant amount of heat can be isolated in another lobe (e.g., the second lobe 215). Such an arrangement can be particularly well suited in instances in which maximum surface temperature is acceptable, but internal temperatures are unsuitable for the operation of electronics components.

In other embodiments, the top cover 210 can be constructed of aluminum, aluminum alloy, or other suitable material having a thermal conductivity higher than typical surgical table bases. For example, the top cover 214 (or a portion thereof) can be constructed of a material having a thermal conductivity of 200 W/m K or greater. In some scenarios, however, aluminum or other conductive material may not be suitable for the top cover 210. For example, such a material may possess insufficient structural support for the column 270. In some such embodiments the top 214 can be constructed of a steel casting, and a side wall 218 (or a portion thereof) can be constructed of aluminum, copper, or other suitable material.

Figure 4:
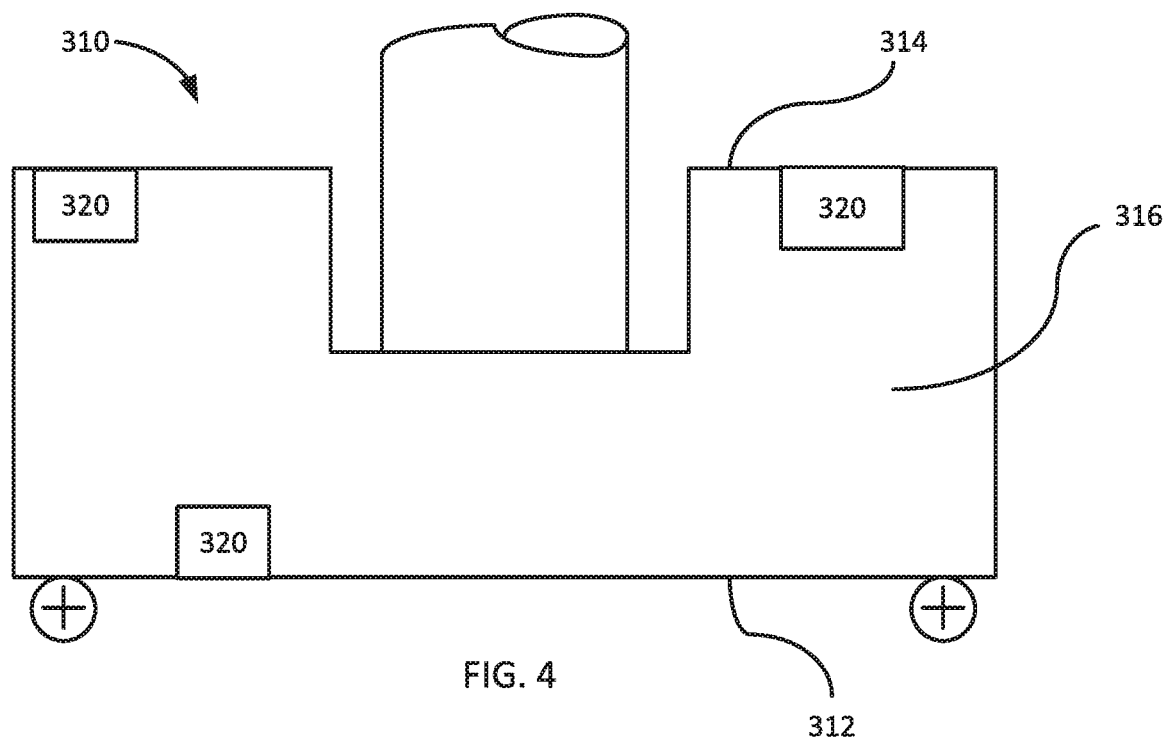
FIG. 4 is a schematic side view of a base of a surgical table having electronic components coupled to a top of the base, according to an embodiment.

FIG. 4 is a schematic side view of a base 310 of a surgical table having electronic components 320, according to an embodiment. The base 310 and/or the electronic components 320 can be structurally and/or functionally similar to the bases 110, 210 and the electronic components 110, 210, respectively, described above.

Traditionally, surgical tables including electronic components in the base located such electronic components on the bottom plate of the base. In embodiments in which a relatively small amount of waste heat is generated, such an arrangement may be suitable. In embodiments in which the electronic components 320 include power electronics for surgical robots and/or generate significantly more (e.g., ~150 W) waste heat than traditional surgical table electronics (e.g., ~40 W), such arrangement may not adequately reject waste heat.

As shown in FIG. 4, one or more electronic components 320 can be coupled to a top cover 314 of the base 310. In some instances, relatively high waste-heat producing electronic components 320 (e.g., transformers) can be coupled to the top cover 314 such that they can more efficiently reject heat through the top cover 314 to the outside environment, relative to being disposed on the bottom plate 312, which may result in relatively more heat being trapped within the interior volume 316. In some such embodiments, electronic components that are relatively sensitive to heat (e.g., batteries) are disposed on the bottom plate 312, which can be relatively cooler.

Figure 5:
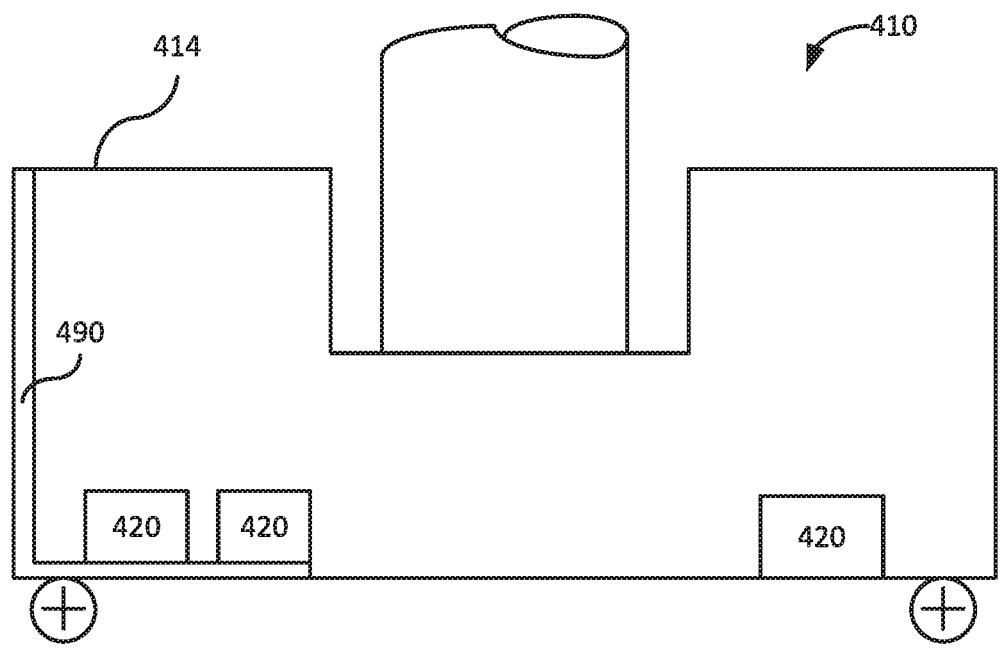
FIG. 5 is a schematic side view of a base of a surgical table having electronic components and a passive heat transfer element, according to an embodiment.

FIG. 5 is a schematic side view of a base 410 of a surgical table having electronic components 420 and a passive heat transfer element 490, according to an embodiment. In some embodiments, a strip or pipe of relatively high conductive material, such as copper can be thermally coupled to one or more electronic components 420 and the top cover 414. Similarly stated, a first end portion of the passive heat transfer element 490 can be thermally coupled to one or more electronic components, while another, opposite, end portion can be thermally coupled to the top cover 414, top-most portion of the base 410, and/or portion of the base 410 constructed of material that is more conductive than steel castings. The passive heat transfer element 490 can be constructed of copper, for example, and have a thermal conductivity of 350 W/m K or more. In some embodiments the heat transfer element 490 can be a heat pipe.

Figure 6:
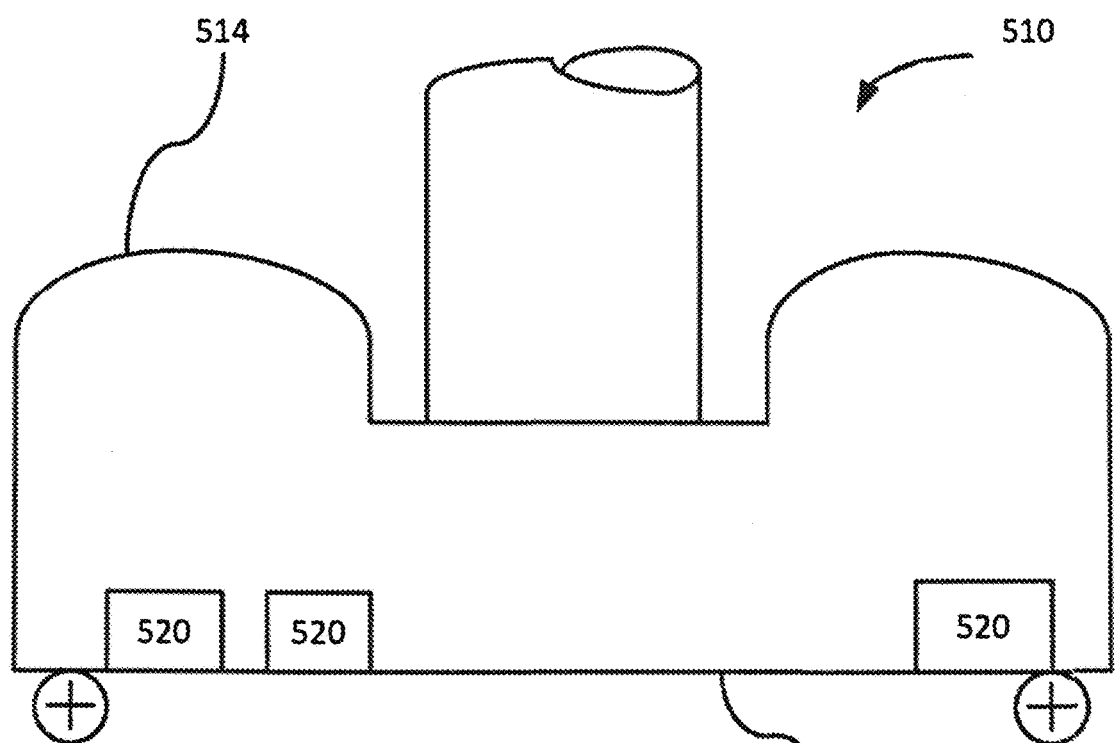
FIG. 6 is schematic side view of a base of a surgical table having an increased surface area, according to an embodiment.
Figure 7:
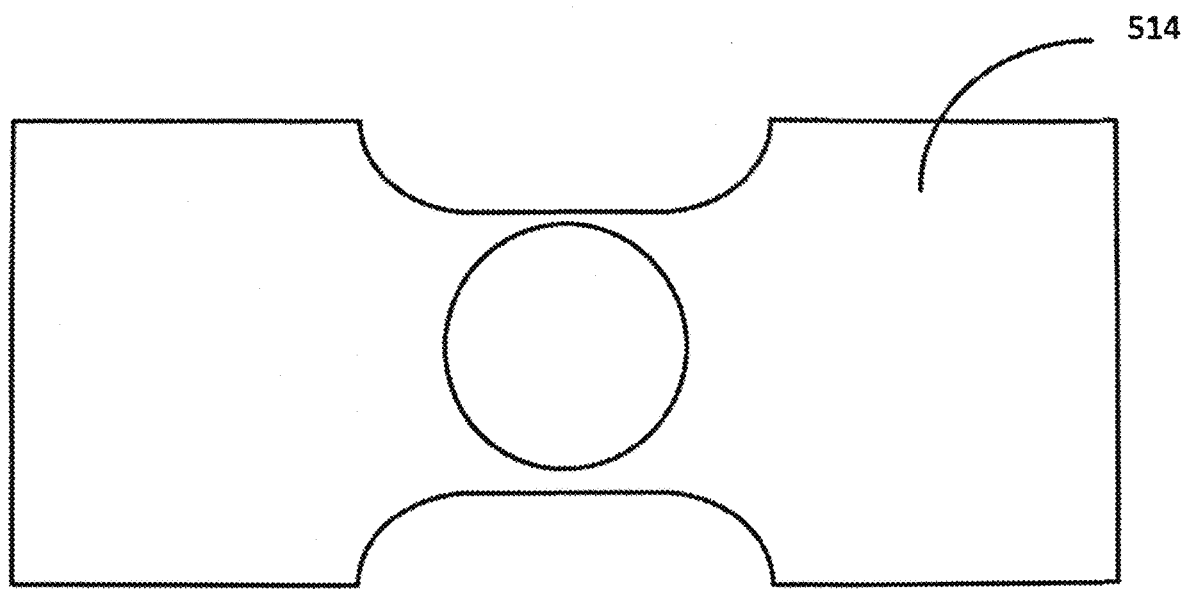
FIG. 7 is a top plan view of the base of the surgical table of FIG. 6.

FIG. 6 is schematic side view of a base 510 of a surgical table, and FIG. 7 is a top plan view of the base 510, according to an embodiment. The base 510 includes a bottom plate 512, a top cover 514, and electronic components 520, each of which can be structurally and/or functionally similar to bases 110, 210, 310, 410, bottom plates 212, 312, top covers 214, 314, and/or electronic components 120, 220, 320, 420, respectively.

As shown in FIG. 6, the top cover 514 is domed, increasing its surface area, which can result in more efficient rejection of waste heat. In some instances, such a domed top cover 514 (or top cover 512 having an increased surface area via similar means) can have a surface area of at least 1.5 times a projected area in a top plan view, such as is shown in FIG. 7.

Figure 8:
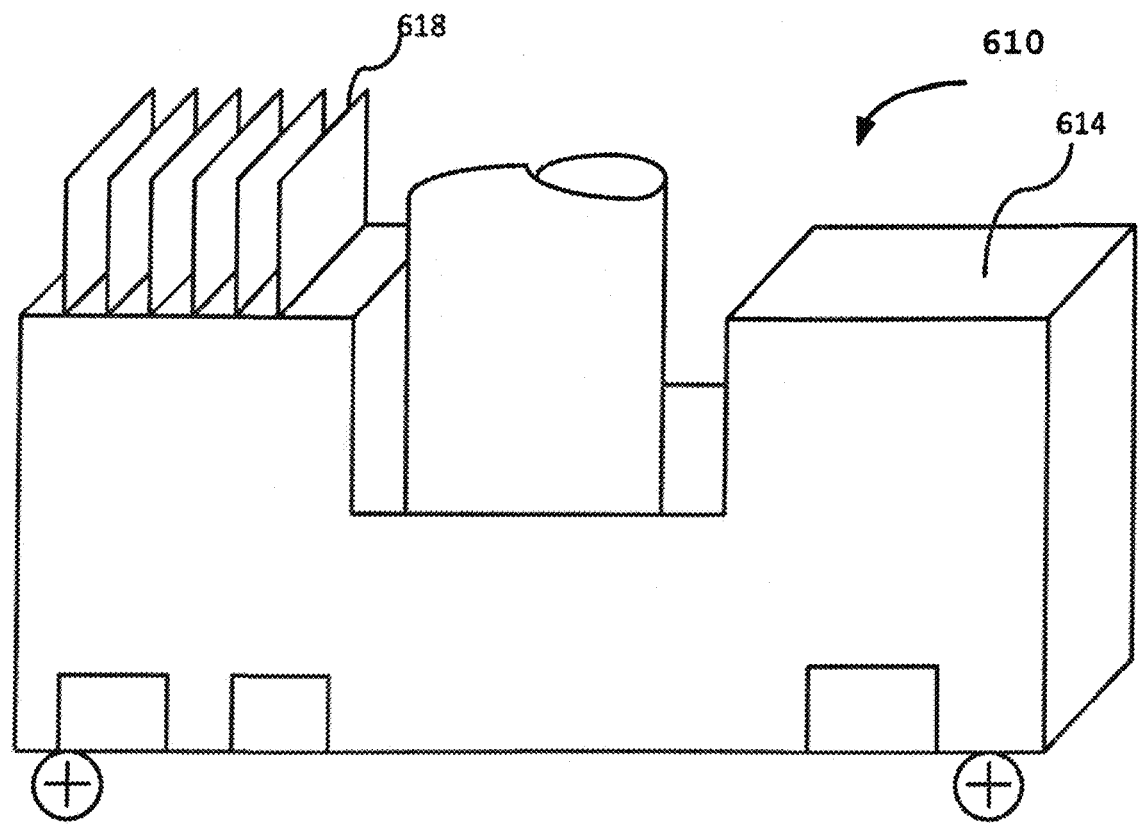
FIG. 8 is schematic perspective view of a base of a surgical table having an increased surface area, according to an embodiment.
Figure 9:
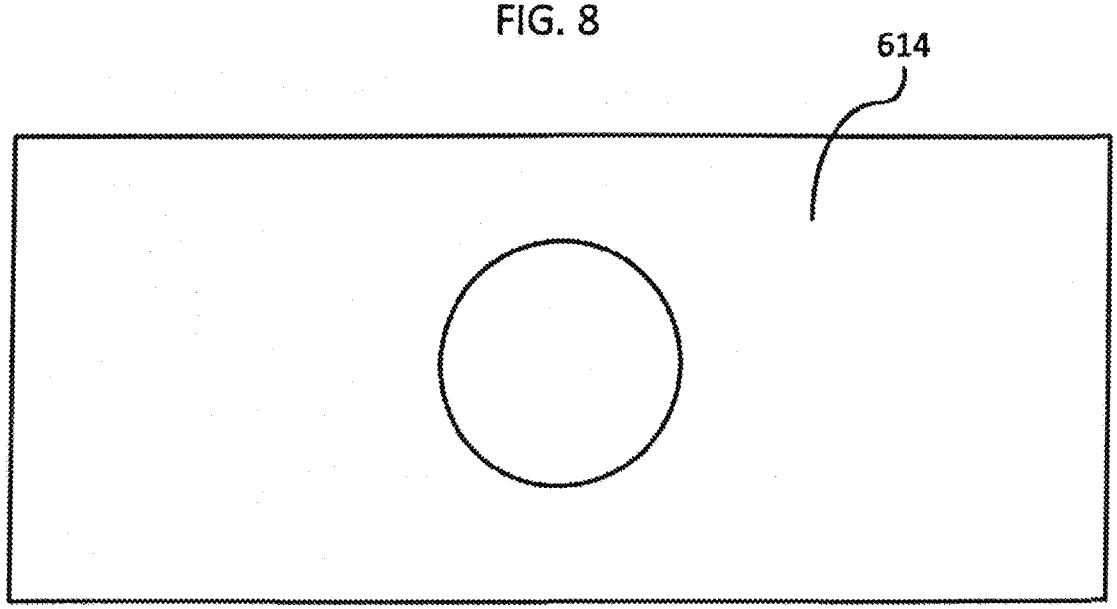
FIG. 9 is a top plan view of the base of the surgical table of FIG. 8.

FIGS. 8 and 9 depict an embodiment a base 610 of a surgical table having increased heat transfer features similar to those discussed with reference to FIGS. 6 and 7. FIGS. 8 and 9 the base 610 and other features depicted in FIGS. 8 and 9 can be structurally and/or functionally similar to similar bases and structures described in further detail herein. The base 610 includes a top cover 612 that includes heat-transfer fins 618. The heat transfer fins 618 can effectively increase the surface area of the top cover 612, improving the ability of the base 610 to reject waste heat. In some such instances, a top cover 612 having fins 618 can have a surface area of at least 2.5 times a projected area in a top plan view, such as is shown in FIG. 9.

While various embodiments have been described herein, it should be understood that they have been presented by way of example only, and not limitation. Furthermore, although various embodiments have been described as having particular features and/or combinations of components, other embodiments are possible having a combination of any features and/or components from any of embodiments where appropriate as well as additional features and/or components. For example, heat transfer strips, such as those described with reference to FIG. 5 can be combined with covers and/or sidewalls constructed of aluminum or similar material, as discussed with reference to FIGS. 2 and 3, fins, as discussed with reference to FIGS. 8 and 9, and so forth.

What is claimed is:

1. A base of a surgical table comprising:
   the base of the surgical table coupled to a surgical table top through a column, the base comprising:
   an enclosure defined by a cover, a bottom and a sidewall, the cover is sealed to the bottom by the sidewall and constructed of a material that is operable to support the column, the surgical table top and one or more surgical robotic arms;
   one or more power electronics components configured to supply power to the one or more surgical robotic arms, the one or more power electronics components are mounted to the bottom within the enclosure,
   a first end portion of a heat transfer element disposed between the one or more power electronics components and the bottom of the enclosure, a second end portion of the heat transfer element disposed proximate to the cover, the heat transfer element selected from a group consisting of a heat pipe and a heat transfer strip constructed of a material having a thermal conductivity greater than a thermal conductivity of the material of the cover and a material of the sidewall.

2. The base of the surgical table of claim 1, wherein the cover, the bottom, and the sidewall of the base define an airtight interior volume within the enclosure, and the material of the cover has a thermal conductivity of at least 200 W/m K.

3. The base of the surgical table of claim 1, wherein the enclosure is airtight such that heat generated by the one or more power electronics components is not transferred to an outside of the enclosure via convection.

4. The base of the surgical table of claim 1, wherein a portion of the cover has a surface area at least 1.5 times an area of the portion of the cover as viewed in a top plan projection of the cover.

5. The base of the surgical table of claim 1, wherein a portion of the cover includes cooling fins such that a surface area of the portion of the cover has a surface area at least 2.5 times the area of the portion of the cover as viewed in a top plan projection of the cover.

6. The base of the surgical table of claim 1, wherein: a portion of the cover includes cooling fins; the second end portion of the heat transfer element coupled to the portion of the cover that includes the cooling fins.

7. The base of the surgical table of claim 1, wherein one or more power additional electronics components are mounted to the cover and do not contact the bottom.

8. The base of the surgical table of claim 1, wherein the cover, the bottom and the sidewall of the base define an airtight interior volume within the enclosure, the cover is constructed of a substantially flat steel casting sealed to the sidewall, and the material of the sidewall has a predefined threshold of thermal conductivity sufficient to reject waste heat generated by the one or more power electronic components.

9. The base of the surgical table of claim 8, wherein the predefined threshold of thermal conductivity comprises a thermal conductivity of at least 200 W/m K.

10. The base of the surgical table of claim 1, further comprising: a fan disposed within the enclosure and configured to induce forced convection within the base.

11. The base of the surgical table of claim 1, wherein: the one or more power electronics components comprise a first power electronics component and a second power electronics component; wherein the second power electronics component is a battery configured to provide uninterrupted power to the one or more surgical robotic arms; and wherein the sidewall is configured to maintain a temperature of the battery below 48° C. while the first and second power electronics components produce at least 150 W of heat.

12. The base of the surgical table of claim 1, wherein:
   the one or more power electronics components comprise a plurality of power electronics components; and
   wherein the sidewall is configured to maintain a maximum temperature of an exterior surface of the base of the surgical table below 45° C. while the plurality of power electronics components produce at least 150 W of heat.

13. The base of the surgical table of claim 1, wherein the cover comprises a first lobe, a second lobe, and an upper-middle portion disposed between the first lobe and the second lobe, the upper-middle portion having a width smaller than a width of the first lobe and a width of the second lobe; the bottom comprises a third lobe disposed below the first lobe of the cover, the first and third lobes defining a first volume of the base, a fourth lobe disposed below the second lobe of the cover, the second and fourth lobes defining a second volume of the base, and a lower-middle portion disposed below the upper-middle portion of the cover the upper-middle and lower-middle portions defining a middle volume of the base, and wherein the middle volume of the base is configured to inhibit airflow between the first volume and the second volume; and the one or more power electronics components are disposed in at least one of the first volume or the second volume.

14. The base of the surgical table of claim 13 wherein the one or more power electronics components includes is a first power supply disposed in the first volume and configured to supply the power to a first one of the one or more surgical robotic arms and a second power supply disposed in the second volume and configured to supply the power to a second one of the one or more surgical robotic arms.

15. The base of the surgical table of claim 13, further comprising: a fan configured to move air between the first volume and the second volume when a temperature of the first volume is greater than a temperature of the second volume.

16. The base of the surgical table of claim 13, wherein the material of the cover has a thermal conductivity of at least 200 W/m K.

17. The base of the surgical table of claim 14, wherein a first subset of the plurality of power electronics components including the first power supply is disposed in the first volume and a second subset of the plurality of electronics components including the second power supply is disposed in the second volume, the first subset of the power electronics components configured to output a greater amount of heat than the second subset of the power electronics components, the base further comprising: a fan configured to move air between the first volume and the second volume.

18. The base of the surgical table of claim 13, wherein the cover is sealed to the bottom forming an airtight enclosure such that heat generated by the one or more power electronics components is not transferred to an outside of the base via convection.

19. The base of the surgical table of claim 1, wherein when the heat transfer element is the heat transfer strip, the material of the heat transfer strip has a thermal conductivity of at least 350 W/m K.

* * * * *